(12) United States Patent
Gabillet

(10) Patent No.: US 12,403,089 B2
(45) Date of Patent: *Sep. 2, 2025

(54) CARRIER FOR THE ORAL ABSORPTION OF AN ACTIVE SUBSTANCE BY ANIMALS, METHOD FOR PREPARING SAME AND USES THEREOF

(71) Applicant: GALEWPET, Loudeac (FR)

(72) Inventor: Hervé Gabillet, Lanouee (FR)

(73) Assignee: GALEWPET, Loudeac (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/073,175

(22) Filed: Dec. 1, 2022

(65) Prior Publication Data

US 2023/0100269 A1 Mar. 30, 2023

Related U.S. Application Data

(62) Division of application No. 16/319,656, filed as application No. PCT/FR2017/050121 on Jan. 20, 2017, now Pat. No. 11,628,140.

(30) Foreign Application Priority Data

Jul. 19, 2016 (FR) ...................................... 1656867

(51) Int. Cl.
*A61K 9/00* (2006.01)
*A23K 20/147* (2016.01)
(Continued)

(52) U.S. Cl.
CPC .......... *A61K 9/0056* (2013.01); *A23K 20/147* (2016.05); *A23K 20/158* (2016.05);
(Continued)

(58) Field of Classification Search
CPC .... A61K 9/0056; A61K 9/5089; A61K 47/12; A61K 50/42; A61K 47/26; A61K 47/36;
(Continued)

(56) References Cited

U.S. PATENT DOCUMENTS 4,362,748 A 12/1982 Cox
2003/0129295 A1 7/2003 Richardson
(Continued)

FOREIGN PATENT DOCUMENTS

EP 0320320 A2 6/1989
EP 0796565 A1 9/1997
(Continued)

OTHER PUBLICATIONS

International Search Report and Written Opinion dated Mar. 24, 2017 issued in International Application No. PCT/FR2017/050121 with English translation.
(Continued)

*Primary Examiner* — Trevor Love
(74) *Attorney, Agent, or Firm* — KENEALY VAIDYA LLP

(57) ABSTRACT

The present invention relates to a carrier for facilitating the oral ingestion of at least one active substance by animals, characterized in that it comprises:
  at least one bead comprising said at least one active substance,
  a gelled appetizing matrix surrounding said at least one bead, the pH of said matrix being less than 4,
  wherein the Aw (residual water) of said matrix and of said at least one bead is identical and from 0.4 to 0.9. The present invention also relates to a method for preparing such a carrier, and also to the uses thereof. The present
(Continued)

invention also relates to a non-therapeutic method for feeding animals, in particular dogs and cats, by means of this carrier.

11 Claims, 6 Drawing Sheets

(51) Int. Cl.
| | |
|---|---|
| *A23K 20/158* | (2016.01) |
| *A23K 20/163* | (2016.01) |
| *A23K 40/20* | (2016.01) |
| *A23K 40/30* | (2016.01) |
| *A23K 50/42* | (2016.01) |
| *A61K 9/50* | (2006.01) |
| *A61K 47/12* | (2006.01) |
| *A61K 47/26* | (2006.01) |
| *A61K 47/36* | (2006.01) |
| *A61K 47/42* | (2017.01) |
| *A61K 47/44* | (2017.01) |

(52) U.S. Cl.
CPC ............ *A23K 20/163* (2016.05); *A23K 40/20* (2016.05); *A23K 40/30* (2016.05); *A23K 50/42* (2016.05); *A61K 9/5089* (2013.01); *A61K 47/12* (2013.01); *A61K 47/26* (2013.01); *A61K 47/36* (2013.01); *A61K 47/42* (2013.01); *A61K 47/44* (2013.01)

(58) Field of Classification Search
CPC ...... A61K 47/42; A61K 47/44; A23K 20/147; A23K 20/158; A23K 20/163; A23K 40/20; A23K 40/30; A23K 50/42
See application file for complete search history.

(56) References Cited

U.S. PATENT DOCUMENTS

| | | |
|---|---|---|
| 2008/0044481 A1 | 2/2008 | Harel |
| 2011/0097427 A1 | 4/2011 | Ramakrishnan et al. |

FOREIGN PATENT DOCUMENTS

| | | |
|---|---|---|
| WO | 2009095417 A1 | 8/2009 |
| WO | WO2016020217 A1 | 2/2016 |

OTHER PUBLICATIONS

T.P. Labuza et al., "Moisture migration and control in multi-domain foods", Trends in Food Science and Technology, vol. 9, No. 2, 1998, pp. 47-55.

CARRIER FOR THE ORAL ABSORPTION OF AN ACTIVE SUBSTANCE BY ANIMALS, METHOD FOR PREPARING SAME AND USES THEREOF

CROSS REFERENCE TO RELATED APPLICATION(S)

This application is a divisional of U.S. patent application Ser. No. 16/319,656 filed on Jan. 22, 2019, which is a national phase filing under 35 C.F.R. § 371 of and claims priority to PCT Patent Application No. PCT/FR2017/050121, filed on Jan. 20, 2017, which claims priority to French Patent Application No. 1656867 filed on Jul. 19, 2016, the contents of each of which are hereby incorporated in its entirety by reference.

TECHNICAL FIELD

The present invention relates to a carrier for facilitating the oral ingestion of at least one active substance by animals, and also to the method for preparing same and to uses thereof.

The present invention has applications in the veterinary field, particularly in the field of animal nutrition and of veterinary medicine.

In the description below, the references between square brackets ([ ]) refer to the list of references presented at the end of the text.

PRIOR ART

The number of domestic animals such as dogs and cats is constantly increasing. In parallel with this increase, there is a change in the care provided to these animals.

However, the treatments administered are not always followed well, because of the difficulty in making the animal take the medicinal substances. It is in fact well known that many of these substances have a repellent effect on the sense of smell of dogs or cats, which refuse to take them, thus making it very difficult or even impossible to comply with a treatment.

There is therefore a need for active substances to be packaged in a form which is capable of evading the vigilance of animals, in particular dogs, cats, horses, pigs and ruminants.

Document EP 0 320 320 ([1]) discloses a tablet comprising a core, containing the active substances, and an appetizing matrix completely surrounding this core. However, this product is difficult to produce because it is not feasible to extemporaneously coat in single units delivered medicaments that have no appetizing matrix.

Document EP 0 574 301 ([2]) describes moreover a pellet consisting of a matrix made of an appetizing material comprising a housing of a shape substantially complementary to that of the tablet to be swallowed by the animal. The tablet is wedged into the housing and then the pellet is presented to the animal in such a way as to hide the tablet. Such a pellet has several drawbacks. Firstly, the pellet is produced with its housing. It is no longer then possible to modify the shape of the latter, in particular to adapt it to tablets of different shapes. Secondly, if the animal bites into the pellet, it can break it and cause the detachment of the active substance. The animal can then feel this active substance and spit it out.

There is therefore a real need for a product which overcomes these faults, drawbacks and obstacles of the prior art, in particular which makes it possible to facilitate the oral ingestion of at least one substance by animals.

DESCRIPTION OF THE INVENTION

After considerable research, the Applicant has managed to develop a carrier which makes it possible to overcome the drawbacks.

The carrier of the invention advantageously makes it possible to facilitate the oral ingestion of at least one substance by animals, and more advantageously of two or more than two active substances simultaneously by animals.

Surprisingly, the carrier of the invention allows in particular the simultaneous ingestion of substances of which the administration is generally considered incompatible, such as for example essential oils and probiotics.

In addition, the carrier of the invention advantageously makes it possible to retain stably, from a bacteriological point of view, one or more active substances within it, in particular without the active substances being mixed together.

The carrier of the invention is particularly advantageously spontaneously taken by the animals, despite the fact that it may contain active substances of which the taste, odour or texture in a conventional formulation is not popular with animals.

Thus, a first subject of the invention relates to a carrier for facilitating the oral ingestion of at least one active substance by animals, characterized in that it comprises:
  at least one bead comprising said at least one active substance,
  a gelled appetizing matrix surrounding said at least one bead, the pH of said matrix being less than 4,
  wherein the residual water (Aw) of said matrix and of said at least one bead has an identical value of from 0.4 to 0.9.

The carrier of the invention advantageously has a shape and a size allowing its oral ingestion by an animal. The shape and size can be adjusted according to the animal, in particular according to its nature, its size and/or its age, by those skilled in the art in the light of the general knowledge in this field. By way of example, the shape of the carrier may be that of a bone, a cylinder, a pellet, a dome, a crescent, a parallelepiped, a triangle, a cross, a sphere, a puck, a disc, a star, or a cube, this list not being limiting. The carrier can be presented as a treat for animals, and therefore have a shape and size suitable for this.

For the purposes of the present invention, the term "animals" means animals other than humans. The animals can be domestic animals or livestock, such as for example dogs, cats, domestic mice, domestic rats, hamsters, guinea pigs, gerbils, ferrets, horses, donkeys, cows, llamas, pigs, rabbits, ducks, pigeons, parakeets, peacocks, fish and shellfish. Preferably, the animals may be dogs or cats.

For the purposes of the present invention, the term "active substance" means any active substance having an impact on the health and/or nutrition and/or well-being of the animal. It can be for example a substance:
  allowing the treatment or prevention of a disease of the animal, and/or
  allowing the care, for example for oral hygiene, of the animal, in particular to prevent/reduce tartar and/or to improve the breath of the animal, and/or
  for cosmetic purposes, in particular regarding the coat, for example for improving the shine of the hair, and/or for restoring the hydration of the skin by reinforcing the skin barrier function, and/or for slowing down the fall of the hair (outside seasonal moulting) and supporting regrowth, and/or for reducing the presence of dandruff, and/or for deodorizing the hair while respecting the animal's sense of smell, and/or for protecting the coat by an antioxidant effect, and/or for wellness, for example having an action against stress, and/or against excess weight of the animal, or for improving the digestion of the animal, and/or for improving the tone of the animal, and/or having an action in a post-operative context, for example following a digestive endoscopy, a respiratory endoscopy, a scan, myelography, a myeloscan, a CSF puncture, arthroscopy, an electroretinogram, an orthopaedic radiographic assessment, an x-ray screening for hip dysplasia, or for example following soft-tissue surgery, for example treatment of simple nasal aspergillosis, excision of the ear canal and bullectomy, treatment of brachycephalic breed syndrome, treatment of patent arterial duct, thoracoscopic pericardectomy, pulmonary lobectomy, laparoscopic liver, pancreas or kidney biopsy, portosystemic shunt, bile duct surgery, perineal hernia repair, laparoscopic ovariectomy, elective laparoscopic gastropexy, treatment of the ectopic ureter, incontinence surgery, prostate surgery (cyst, abscess, etc.), skin surgery with skin flap or graft, and/or reconstruction of the chest or abdominal wall, or for example following an ophthalmological surgery, such as treatment for entropion, ectopic eyelid, palpebral papilloma, palpebral tumour and graft, dislocation of the nictitating gland, malposition of the nictitating membrane, Stenon's duct bypass, a corneal wound, a conjunctival graft component, lamellar keratectomy, corneal transplantation, cataract surgery, such as simple phacoemulsification, dislocation of the lens, an endocular prosthesis, strabismus surgery secondary to dislocation of the eyeball, or for example following orthopaedic surgery, for example following a fracture, cruciate ligament rupture, patella dislocation, hip dislocation, osteochondritis dissecans, pelvic osteotomy, total hip prosthesis, or for example neuro-spinal surgery, such as a hemilaminectomy, a corpectomy, or a vertebral dislocation/fracture, or for example following a treatment of a renal disease, such as FLUTD (feline lower urinary tract disease), urolithiasis, acute renal failure (ARF) or idiopathic cystitis.

The substance may in particular be chosen from the group comprising probiotics, essential oils, medicaments, nutraceuticals and nutrients. The carrier of the invention may contain either just one of these active substances or several of these active substances, for example 2 or 3 or 4 or 5.

Among the probiotics, any probiotics that can be used in animals may be involved. They may be, for example, Bifidobacteria, such as *L. acidophilus* and *L. bulgaricus, L. casei* and *Bifidobacterium bifidus, Enterococcus faecium, Saccharomyces cerevisiae* or *Bacillus subtilis*.

Among the essential oils, any essential oil that can be used in animals may be involved. They may be for example ahibéro essential oil, tropical basil essential oil, Roman chamomile essential oil, Chinese cinnamon essential oil, Atlas cedar essential oil, Cistus ladanifer essential oil, lemon (zest) essential oil, Ceylon citronella essential oil, lemon eucalyptus essential oil, mentholated eucalyptus essential oil, wintergreen essential oil, juniper essential oil, rose geranium essential oil, clove essential oil, hyssop essential oil, iary essential oil, immortelle (Helichrysum) essential oil, katafray essential oil, bay laurel essential oil, lavender aspic essential oil, true lavender essential oil, lavandin super essential oil, lemongrass oil, peppermint essential oil, niaouli essential oil, compact oregano essential oil, palmarosa essential oil, ravintsara essential oil, annual tansy essential oil, tea tree essential oil or thyme linalool essential oil.

Among the medicaments, any medicament that can be used in animals may be involved. They may be, for example, anti-infective agents, such as antibiotics or sulfamides, internal and/or external anti-parasitic agents, anti-inflammatories or antihistamines, oral vaccines, hormones, digestive therapy substances, such as gastrointestinal dressings and sedatives, replacement flora, antidiarrhoeals, hepatoprotectants, antispasmodics, laxatives, intestinal antiseptics and oral rehydrators, renal therapy substances, cardiovascular therapy substances such as cardiac and cardiovascular analeptics, haemostatics, vasoconstrictors and dilators, respiratory therapy substances such as respiratory analeptics, antitussives, bronchodilators, bronchosecretolytics and respiratory antiseptics, substances acting on the nervous system such as analgesics, sedatives and tranquillizers, anti-epileptics, anaesthetics, orexigenics and anorexigenics, immune therapy substances such as immunosuppressants, immunostimulants and replacement immunoglobulins, diuretics, anticancer substances such as antimitotics and substances for the treatment of joints, in particular against osteoarthritis, such as glucosamine, chondroitin, or anti-inflammatories.

Among the nutrients, any nutrient that can be used in animals may be involved. They may be for example one or more nutrients chosen from:

vitamins, minerals, such as calcium, phosphorus or magnesium, trace elements, such as iron, zinc, iodine, selenium, copper, chromium, manganese, cobalt or fluorine, proteins, of animal origin, such as egg, meat, fish or milk proteins, or of plant origin, such as soya isolates. These may for example be amino acids, such as arginine, glutamine, tyrosine, phenylalanine, carnitine or taurine, lipids, such as fatty acids, for example omega 3 or omega 6 fatty acids, carbohydrates, such as starch, insoluble fibers such as crude cellulose or lignin, soluble fibers, such as fructooligosaccharides (FOSs) or mannan oligosaccharides (MOSs), or simple sugars or carbohydrates, parts or extracts of plants, for example Aloe vera, *Valeriana officinalis, Passiflora incarnate, Rosmarinus* sp., *Vitis* sp., *Curcuma* sp, Eugenia sp. part or Citrus sp, this list not being limiting, parts or extracts of algae, such as for example *spirulina*.

Among the nutraceuticals, any nutraceutical that can be used in animals may be involved. These may for example be one or more nutraceuticals chosen from: chitosan, glucosamine, chitooligosaccharides and fermented soya.

For the purposes of the present invention, the term "bead" means any container containing an active substance, and substantially spherical in shape. The bead may have a diameter of from about 200 microns to about 6 mm. The bead may be a solid container or a hollow container. If it is a hollow container, it may be for example a capsule, in particular a microcapsule, or a vesicle. Advantageously, it may be a microcapsule containing an active substance, the shape of which is defined by a shell. If it is a solid container, the bead may for example be coated, in particular to maintain the shape of the beads and so that the contents of the beads do not disperse in the matrix. The means for coating the beads may be any means making it possible to obtain this effect, such as, for example, hydrocolloids such as alginate, pectin, and/or melted plant wax.

The residual water content (Aw) of a bead is from 0.4 to 0.9, for example from 0.5 to 0.8, or from 0.55 to 0.75, or from 0.6 to 0.75. Advantageously, the value of 0.9 is excluded from the range. Advantageously, this Aw range allows optimal microbiological stability of the active substance contained in the bead. Those skilled in the art can choose the Aw from these ranges of values depending on the active substance contained in the bead, by means of their general knowledge of the technical field. The Aw can be measured by those skilled in the art by any known method, for example by means of an Aw meter of the Labswift-aw type from Novasina. The Aw can be obtained or controlled by any means known to those skilled in the art, for example by means of at least one humectant chosen from monopropylene glycol and/or xylitol.

The shell of the bead may be any shell for defining the outline of the bead. The shell may in particular make it possible to isolate the inside of the bead from the outside of the bead, that is to say to mechanically limit the exchanges between the inside and the outside of the bead. The shell advantageously allows the Aw of the beads to be preserved.

The shell of the bead may consist of or comprise any material allowing the abovementioned technical effect(s). The bead may for example be a gelled bead, that is to say the shell of which comprises or consists of a gelling agent, for example alginate, such as sodium alginate or calcium alginate, and/or plant wax, for example jojoba oil, carnauba wax, candelilla wax, cera bellina wax, rice wax or soya wax. Preferably, the bead is a capsule or microcapsule of alginate and/or of plant wax. The amount of gelling agent in the bead or its shell may be from 0.1 to 5.0%, for example from 0.3 to 4.5%, or from 1.0 to 4.0%, or from 1.5 to 3.5%.

The shell may comprise one or more dye(s). Thus, a bead may appear coloured. Advantageously, a bead may be coloured depending on the active substance that it contains, in order to identify the nature and/or the number of active substance(s) present per carrier. Advantageously, a bead may be coloured so as to be visible in the matrix, or, conversely, so as not to be visible therein. In the first case, the bead has a colour different from the colour of the matrix. In the second case, the bead has a colour identical or almost identical to that of the matrix. A bead may have a colour chosen from blue, red, green, yellow, pink, orange, purple, brown, black, caramel, white and grey. The matrix may be transparent or opaque, and/or have a colour chosen from blue, red, green, yellow, pink, orange, purple, caramel, brown, black, white and grey.

Advantageously, the carrier of the invention may contain one bead or more than one bead, for example at least 2 beads, for example at least 3, or at least 4, or at least 5 beads, or at least 10 beads, or at least 15 beads, or more, it being possible for their number to depend on their size relative to that of the carrier. For example, the carrier may comprise from 2 to 15 beads, or from 2 to 10 beads, or from 3 to 10 beads, or from 4 to 10 beads, in particular if the diameter of the beads is from 2 mm to 6 mm. Alternatively, if the diameter of the beads is between 200 μm and 2 mm, the number of beads may be greater than 15, or greater than 20, or greater than 50.

Advantageously, a carrier may contain either a single active substance, if the carrier comprises only one bead or if all the beads of the carrier all contain the same active substance, or more than one active substance if the carrier contains several beads which each contain an active substance different from that of the other beads. Thus, the carrier may contain one active substance, or 2 active substances, or at least 2 active substances, for example at least 3 active substances, or at least 4 active substances, or at least 5 active substances, for example 10 active substances.

Each bead may contain an amount of active substance suitable for the needs of the animal to which the carrier is administered. For example, each bead may contain from 20 to 70% by weight of an active substance relative to the total weight of the bead, for example from 30 to 60%, or from 40 to 50%.

The carrier thus comprises a matrix in which one or more beads are distributed. The matrix is therefore a material encompassing one or more beads as defined above.

Advantageously, the matrix may also comprise a material for preventing and/or reducing tartar on the dentition of the animal, by its abrasive effect potentially related to the mechanical characteristics of the material. It may be for example micocrystalline cellulose, such as E 460, for example included in the form of these beads in the matrix. The matrix is an appetizing matrix, of which the texture, consistency, taste and smell are able to make the carrier attractive to an animal and cause said animal to readily eat it.

Advantageously, the taste and smell of the matrix may be appetizing because of the presence in the matrix of appetizing factors. These may be, for example, appetizing factors based on meat or fish or shellfish, or appetizing factors mimicking the taste of meat, fish, shellfish, animal food or dry animal food.

Advantageously, the texture and consistency of the matrix may be appetizing because of its pleasant nature in the mouth and pleasant chewy nature for the animal. The matrix may have, for example, a soft gel-like texture, such as pudding, or custard, or Gummy Bear® gummy candies.

The matrix may be a gelled matrix, comprising a suitable gelling agent, for example chosen from carrageenans, agar agar, gellan gum, beef, pork or fish gelatin, xanthan gum, carob seed flour, guar gum, gum arabic, alginates, gum tragacanth (also called tragacanth) and starches. The amount of gelling agent in the matrix may be from 0.5 to 20%, for example from 1.0 to 18.0%, or from 5.0 to 15.0%, or from 7.0 to 13.0%.

The pH of the matrix is less than or equal to 4.0, or alternatively strictly less than 4.0, for example between 0 and 3.8 or between 0.5 and 3.5, or between 1.0 and 3.0. This pH advantageously allows the carrier to be very stable over time, for example at least 2 years, especially from a microbiological point of view. The pH can be measured by any method known to those skilled in the art, for example by means of a pH meter. The pH can be obtained or controlled by any means known to those skilled in the art, for example by means of at least one organic acid, such as, for example, propionic acid, isovaleric acid or butyric acid.

The residual water (Aw) of the matrix has a value from 0.4 to 0.9, for example from 0.5 to 0.8, or from 0.55 to 0.75, or from 0.6 to 0.75. The value of the Aw is identical to that of the beads. This identity between the Aw of the matrix and the Aw of the beads advantageously makes it possible to avoid exchanges between the contents of the beads and the matrix. In other words, each active substance remains in the bead that contains it and cannot transfer into the matrix. Thus, no active substance can be found in the presence of one or more other active substances in the matrix, nor can it mix in the matrix. The Aw can be measured by those skilled in the art by any known method, such as, for example, the Labswift-aw Aw meter from Novasina. The Aw can be obtained or controlled by any means known to those skilled in the art, for example by means of at least one humectant chosen from monopropylene glycol and/or xylitol.

The carrier of the invention thus makes it possible to contain, and thus to administer, in a single dose, to an animal, several active substances. Advantageously, the carrier of the invention may comprise active substances which, as a general rule, are not compatible for simultaneous administration. The carrier may for example contain a probiotic and an essential oil, each of these substances being in a bead and thus being physically separated from the other, with it being impossible for them to mix.

Another subject of the invention relates to the use of a carrier as defined above, for facilitating the oral ingestion of at least one active substance by animals, said active substance being chosen from probiotics, essential oils, nutraceuticals and nutrients. Such a subject is a non-therapeutic use. Advantageously, the active substance may be at least one nutrient. In this embodiment, the carrier is administered to healthy animals, that is to say animals not affected by a pathological condition, or animals for which the administration of the carrier is not carried out as part of a therapeutic or prophylactic treatment of a pathological condition.

Another subject of the invention relates to a carrier as defined above, for preparing a medicament intended for animals. In this embodiment, the active substance may be chosen from the group comprising probiotics, essential oils, medicaments, nutraceuticals and nutrients. It may preferably be medicaments. In this embodiment, the carrier is administered to healthy animals or animals suffering from a pathological condition, and the administration of the carrier is carried out as part of a therapeutic or prophylactic treatment of a pathological condition in these animals.

Another subject of the invention relates to a method for preparing a carrier as defined above, comprising the following steps:
1) encapsulating at least one active substance by (i) bringing said at least one active substance into contact with an encapsulation solution, (ii) mixing said encapsulation solution in a gelling bath and (iii) extruding the mixture in the form of beads,
2) preparing said gelled matrix by (i) mixing the components of said matrix and a gelling agent, (ii) heating said mixture to the hydration temperature of said gelling agent, (iii) cooling the mixture for it to be cast into a mould,
3) casting the mixture obtained in step 2) into said mould and introducing said beads into said mould, this allowing to obtain said carrier.

The first step of the method of the invention therefore allows the encapsulation of at least one active substance in the form of beads as defined above. In this step, the encapsulation solution may be any solution allowing the formation of a shell around the active substance. The encapsulation solution may for example be composed of alginates and/or of plant wax. The encapsulation solution may also comprise any other suitable compound, for example one or more ingredients chosen from dyes and bulking agents, such as starches. The gelling bath makes it possible to gel the encapsulation substance and to give it the shape of a shell around the active substance. The gelling bath may be composed of any suitable substance known to those skilled in the art, such as for example calcium chloride and/or citric acid. The gel bath comprising the encapsulation solution and the active substance is then subjected to an extrusion step to give the mixture the shape of beads. The extrusion can be carried out by any suitable method known to those skilled in the art, such as for example by dripping into the gelling bath. Finally, the beads formed can be filtered and then rinsed and dried.

In the case where it is desired to prepare a carrier containing several kinds of active substances, each bead containing a particular active substance is made independently of the others by carrying out step 1) of the method. In other words, the various active substances are not mixed in step 1), but are encapsulated independently of one another by the independent implementation of step 1). Step 1) is therefore carried out as many times as there are different active substances to be encapsulated. The steps 1) can be carried out successively.

The second step of the method of the invention is the preparation of the matrix as defined above. The components of the matrix are first of all mixed with at least one gelling agent as described above. Then, the mixture composed of the components of the matrix and the gelling agent(s) is heated up to the hydration temperature of the gelling agent. Advantageously, the mixture gradually thickens while reaching the gelation temperature which is lower than the hydration temperature. This hydration temperature, which is the temperature T° C. at which the properties of the gelling agent are activated, is a physical parameter known to those skilled in the art, who may determine it according to the compounds present in the mixture. In general, the hydration temperature is between 75 and 90° C., depending on the gelling agents. Finally, the mixture is cooled until its consistency is suitable for it to be cast into a mould. Advantageously, citric acid and/or propionic acid and/or butyric acid and/or isovaleric acid may be used to lower the pH.

In the first step and in the second step, the Aw can be controlled by adding at least one humectant, such as for example monopropylene glycol or xylitol.

The third step is the step of casting the cooled mixture into a mould. The mould may have a shape suitable for giving the carrier of the invention the desired shape. Once the mixture has been cast into the mould, the beads are introduced, preferably uniformly, into the mould, that is to say into the mixture constituting the matrix, which makes it possible to obtain a carrier comprising a matrix in which are included beads containing at least one active substance. In order to be able to easily incorporate the beads into the mixture, the beads are introduced therein before the matrix is completely gelled. The carrier having the desired consistency is then obtained by leaving the mixture in which the beads are included to cool.

Another subject of the invention relates to a non-therapeutic method for feeding animals, in particular dogs and cats, comprising the following operations:
a) production of a carrier as defined above, and
b) administration of said carrier to said animals.
In this context, the carrier does not contain medicaments or any active substance capable of treating or preventing a pathological condition of an animal.

Other advantages may also become apparent to those skilled in the art on reading the examples below, illustrated by the appended figures and given by way of illustration.

EXAMPLES

Example 1: Production of Jelly Treats

Figure 1:
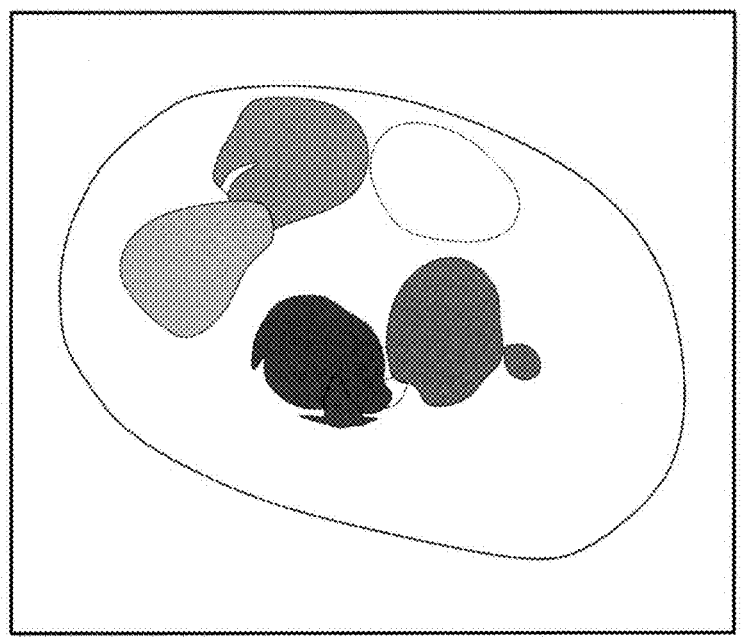
FIG. 1 shows a top view of a transparent carrier of oval shape comprising 5 beads of different colours.
Figure 2:
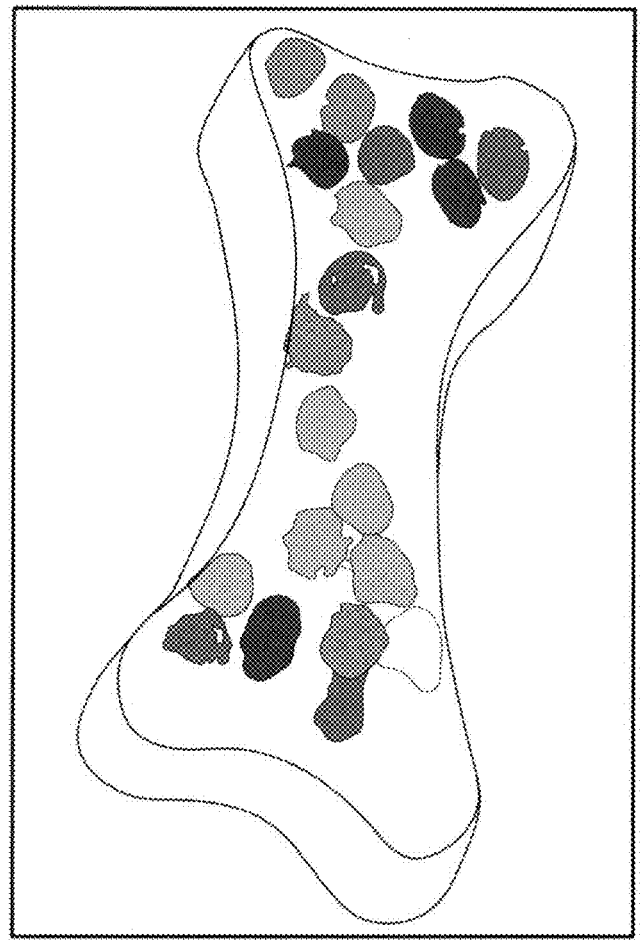
FIG. 2 shows a top view of a transparent carrier in the shape of a bone comprising 20 beads of different colours.

The first step of the production method consists in the encapsulation of active materials in the form of beads of alginates or of plant wax. These beads comprise between 20 and 70% of active materials and have a diameter of from 200 microns to 6 mm. Their Aw (residual water) is between 0.4 and 0.9.

The production of the beads consists of the preparation of an encapsulation solution composed of alginates or plant wax.

The gelling bath is then prepared. This consists of CaCl$_2$) and citric acid.

The active agents and also the bulking agents (starches) and the dyes are incorporated into the encapsulation solution. The mixture is then extruded by dripping into the gelling bath.

Finally, the beads formed are filtered and then rinsed and dried on a fluidized air bed (70° C.).

The second step consists of the preparation of 2 mixtures.

A 1$^{st}$ mixture comprising all the liquid raw materials of the composition is prepared. Said mixture is composed of glucose syrup, glycerol, water, appetizing factor and oil (plant or fish oil). This mixture is heated until complete dissolution of the thicker raw materials.

A 2$^{nd}$ mixture comprising the raw materials in powder form is prepared. Said mixture contains the gelling agent (carrageenans, agar agar, gellan gum, beef, pork or fish gelatin, xanthan gum, carob seed flour, guar gum, gum arabic, alginates, gum tragacanth or starches), the appetizing solution, potassium sorbate, sodium citrate, tripotassium citrate, salt, dextrose.

The various liquid ingredients (water, glucose syrup, glycerol) of the matrix are dissolved and heated until complete dissolution of the liquid raw materials. When all the liquids have melted, the powdered raw materials core is introduced.

The mixture is then brought to the hydration temperature of the gelling agent used (between 75 and 90° C.).

The temperature of the mixture is then allowed to drop back to 70° C. and the citric acid is introduced.

The mixture is allowed to cool and is left to increase slightly in viscosity.

The mixture is then poured into blisters and the beads containing the different active materials are introduced into each Gelicaps, and uniformly distributed.

Example 2: Carrier Composition Example

A carrier of the invention, presented as a dog treat, is prepared by carrying out the method described in step 1, and has the following composition:

Beads:

|  | PERCENTAGE BY WEIGHT IN THE BEAD |
|---|---|
| Alginates | 0.1% to 5% |
| Starches | 2% to 50% |
| Dyes | 0.05% to 2% |
| Active substance | 10% to 90% |

Matrix:

| | |
|---|---|
| Water | 30.775% |
| Glucose syrup | 20% |
| Glycerol | 18% |
| Appetizing factor | 5% |
| Fish oil | In the 1% coating or in the matrix |
| Brief gelatin | 12.5% |
| Potassium sorbate | 0.4% |
| Sodium citrate | 0.1% |
| Tripotassium citrate | 0.075% |
| Salt | 2% |
| Dextrose | 9.55% |

Example 3: Change in the Stability of the Carrier as a Function of pH

Carriers were prepared according to the protocol described in Example 1, while at the same time controlling the pH and the Aw of the matrix and of the beads of each of these carriers. For all the carriers, the Aw values are identical in the beads and in the carrier. The pHs obtained have the following values: 3.0, 3.5, 4.0, 4.5, 5.0, 5.5, 6.0.

The Aw is controlled by controlling the amount of glycerol and/or xylitol. For each pH value of the matrix, 8 carriers are prepared in which the liquid ingredients of the matrix and the Aw are described in the following table:

| Glycerol (grams) | Xylitol (grams) | Water (grams) | Aw |
|---|---|---|---|
| 500 | | 1000 | 0.90 |
| 750 | | 1000 | 0.855 |
| 900 | | 1000 | 0.824 |
| 1350 | | 1000 | 0.80 |
| 1350 | 900 | 1000 | 0.715 |
| 1100 | 600 | 1000 | 0.785 |
| 1100 | 900 | 1000 | 0.754 |
| 1500 | 900 | 1000 | 0.692 |

The stability of each carrier is then tested, by inoculating each carrier with the following strains: *Aspergillus amstelodami*, *Aspergillus niger*, *Penicillium verrucosum* and *Candida krusei*.

The cultures were carried out at 25° C., in the dark, for 15 days. Regarding moulds, inoculation is carried out by the peripherry of a growing thallus (the tests focused on the measurement of thallus growth); yeasts were inoculated in drops (containing about $10^6$ CFU/ml), that is to say about $10^3$ CFU.

Figure 3:
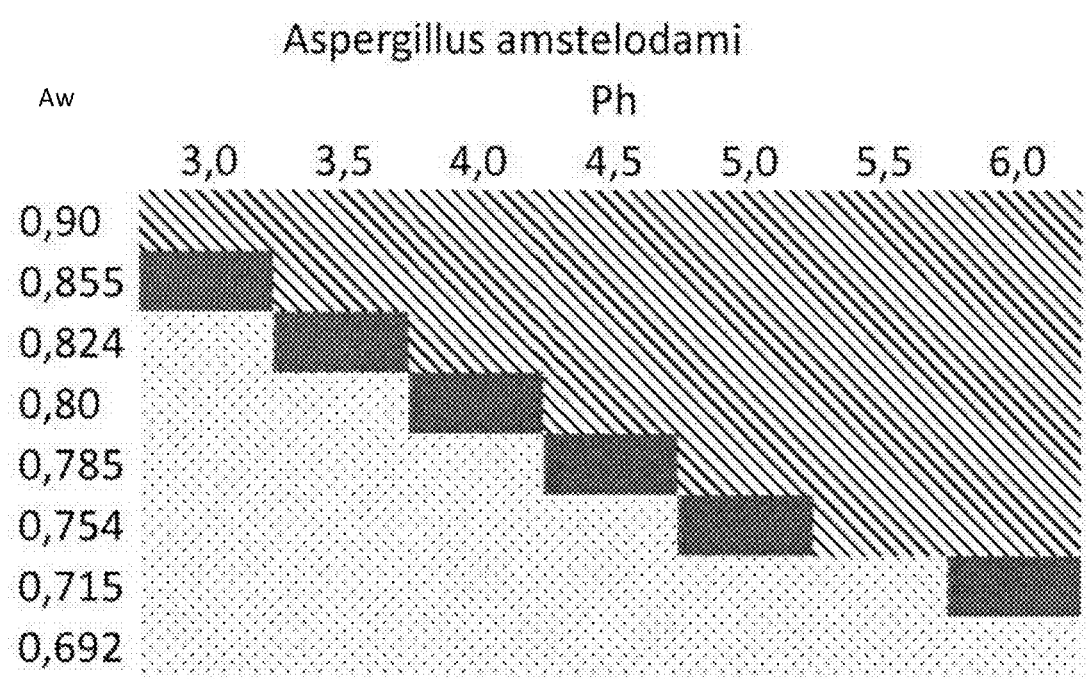
FIG. 3 shows the development of *Aspergillus amstelodami* in a carrier as a function of the pH of the matrix (abscissa) and the Aw (ordinate) of the matrix and the beads. The hatching represents a growth of *Aspergillus amstelodami*, the dots represent an absence of *Aspergillus amstelodami* growth and the grey areas a weak or very slow growth of *Aspergillus amstelodami*.
Figure 4:
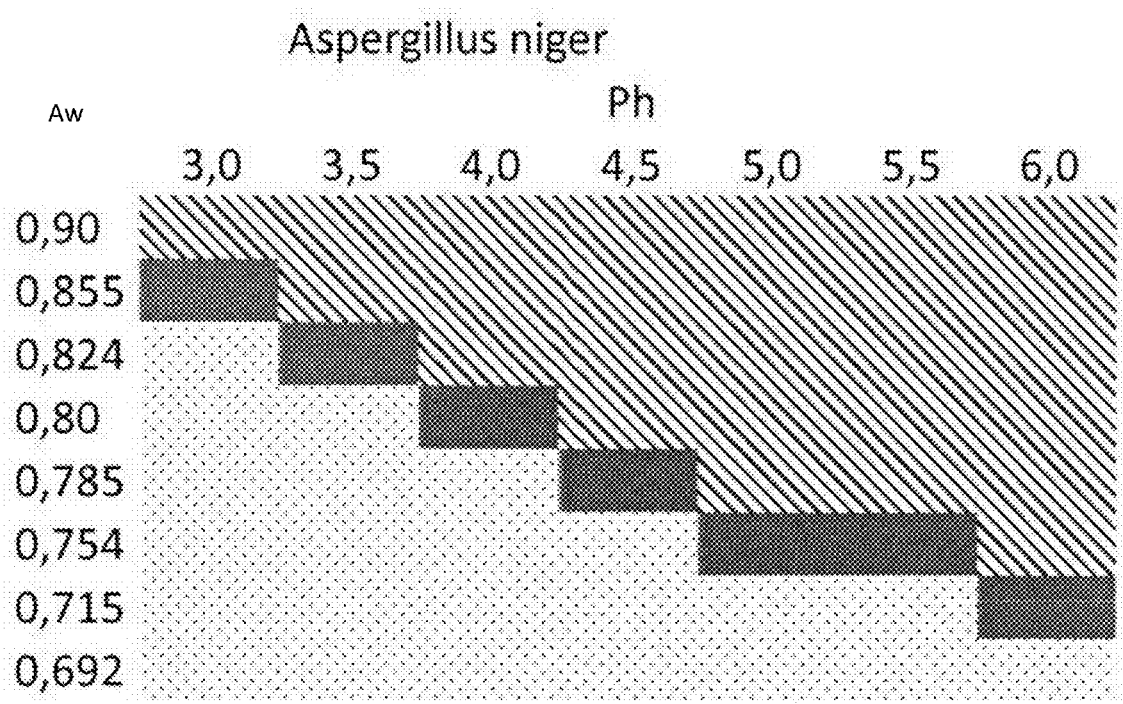
FIG. 4 shows the development of *Aspergillus niger* in a carrier as a function of the pH (abscissa) and the Aw (ordinate) of the matrix and the beads. The hatching represents a growth of *Aspergillus niger*, the dots represent an absence of *Aspergillus niger* growth and the grey areas a weak or very slow growth of *Aspergillus niger*.
Figure 5:
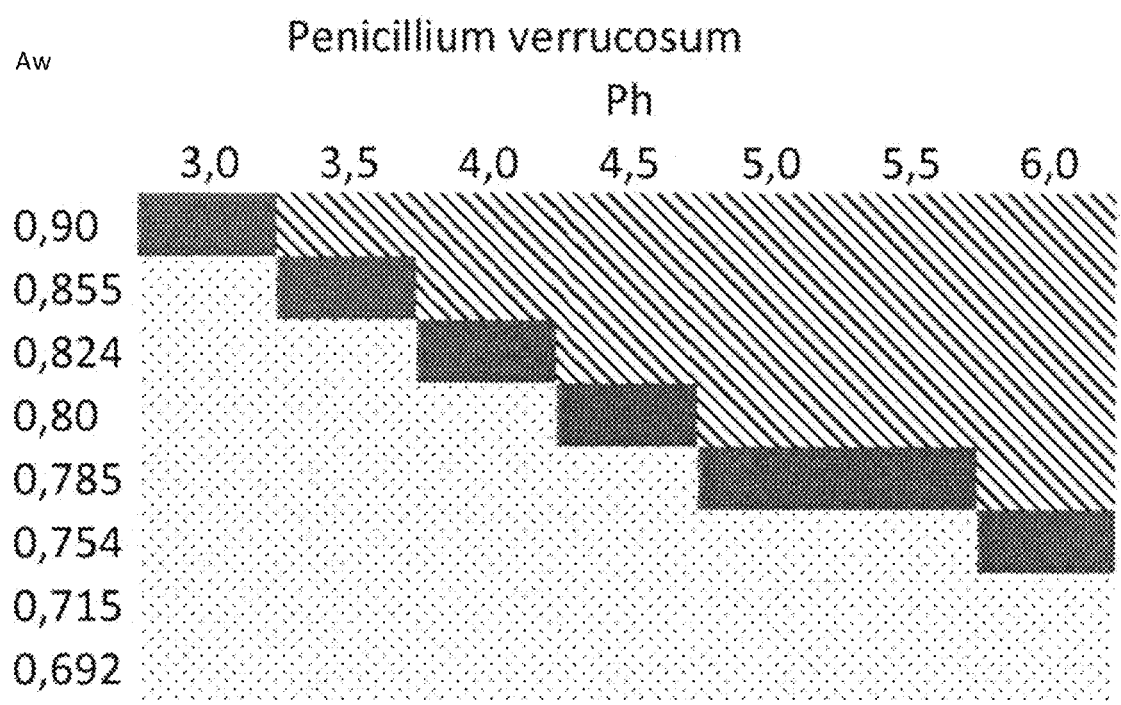
FIG. 5 shows the development of *Penicillium verrucosum* in a carrier as a function of the pH (abscissa) and the Aw (ordinate) of the matrix and the beads. The hatching represents a growth of *Penicillium verrucosum*, the dots represent an absence of *Penicillium verrucosum* growth and the grey surfaces a weak or very slow growth of *Penicillium verrucosum*.
Figure 6:
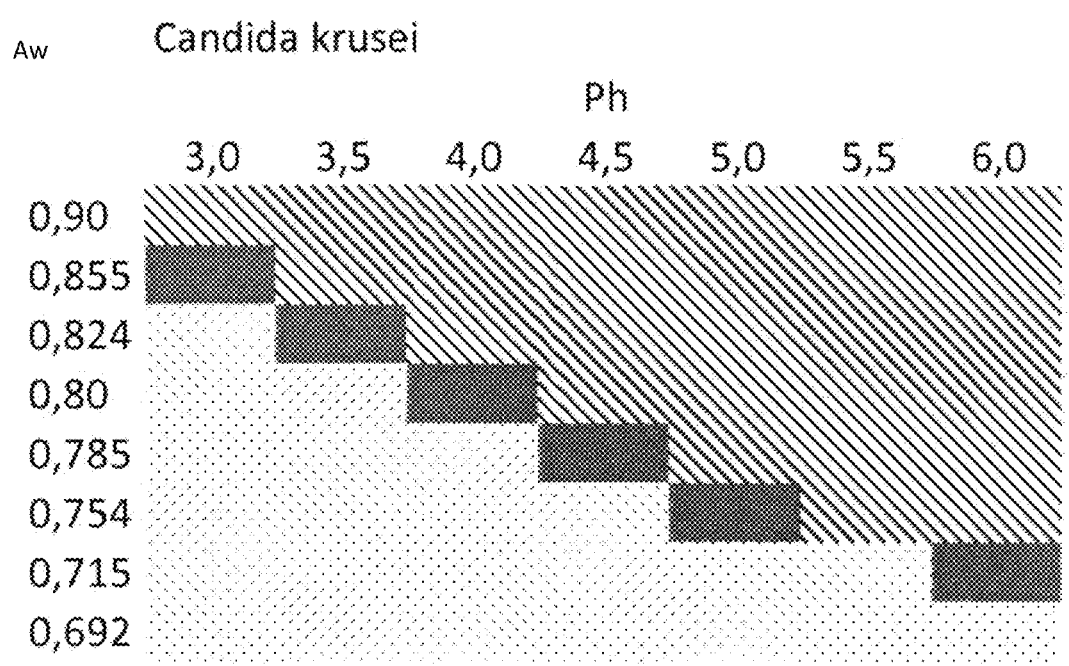
FIG. 6 shows the development of *Candida krusei* in a carrier as a function of the pH (abscissa) and the Aw (ordinate) of the matrix and the beads. The hatching represents a growth of *Candida krusei*, the dots represent an absence of *Candida krusei* growth and the grey surfaces a weak or very slow growth of *Candida krusei*.

The results are described respectively in FIGS. 3, 4, 5, and 6. They show stability of the carrier at a pH of less than or equal to 4.0, for all the microorganisms tested.

REFERENCE LIST

1. EP 0 320 320.
2. EP 0 574 301.

The invention claimed is:

1. Carrier for facilitating the oral ingestion of at least two active substances by animals, characterized in that the carrier comprises:
    at least two beads, each of the beads comprising an active substance that is different from those of the other bead(s),
    a gelled appetizing matrix surrounding said beads, the pH of said matrix being less than 4.5,
    wherein the Aw (residual water) of said matrix and of said beads is identical and from 0.4 to 0.9.
2. Carrier according to claim 1, wherein said beads are capsules or microcapsules.
3. Carrier according to claim 2, wherein said capsules or microcapsules are capsules or microcapsules of alginate or plant wax.
4. Carrier according to claim 1, wherein said matrix comprises a gelling agent chosen from carrageenans, agar agar, gellan gum, beef, pork or fish gelatin, xanthan gum, carob seed flour, guar gum, gum arabic, alginates, gum tragacanth and starches.
5. Carrier according to claim 1, wherein said at least one active substance is chosen from the group consisting of probiotics, essential oils, medicaments, nutraceuticals and nutrients.
6. Carrier according to claim 1, wherein said matrix also comprises microcrystalline cellulose.
7. A method for facilitating the oral ingestion of at least two substances by animals comprising administering a carrier as defined in claim 1 to an animal, said at least two substances being chosen from probiotics, essential oils, nutraceuticals and nutrients.
8. The method according to claim 7, wherein said animals may be domestic animals or livestock.
9. Carrier as defined in claim 1, for preparing a medicament intended for animals.
10. Method for preparing a carrier as defined in claim 1, comprising the following steps:
    1) Encapsulating at least two active substances by (i) bringing said at least two active substances into contact with an encapsulation solution, (ii) mixing said encapsulation solution in a gelling bath and (iii) extruding the mixture in the form of beads,
    2) preparing a gelled matrix by (i) mixing the components of said matrix and a gelling agent, (ii) heating said mixture to the hydration temperature of said gelling agent, (iii) cooling the mixture for it to be cast into a mould,
    3) Casting the mixture obtained in step 2) into said mould and introducing said beads into said mould, this allowing to obtain said carrier.
11. Non-therapeutic method for feeding animals, in particular dogs and cats, comprising the following operations:
    a) production of a carrier as defined in claim 1, and
    b) administration of said carrier to said animals.

* * * * *